(12) United States Patent
Alsafadi

(10) Patent No.: US 8,172,576 B2
(45) Date of Patent: May 8, 2012

(54) DECISION SUPPORT SYSTEM FOR SIMULATING EXECUTION OF AN EXECUTABLE CLINICAL GUIDELINE

(75) Inventor: Yasser Alsafadi, Yorktown Heights, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1263 days.

(21) Appl. No.: 11/572,643

(22) PCT Filed: Jul. 21, 2005

(86) PCT No.: PCT/IB2005/052446
§ 371 (c)(1),
(2), (4) Date: Jan. 25, 2007

(87) PCT Pub. No.: WO2006/013515
PCT Pub. Date: Feb. 9, 2006

(65) Prior Publication Data
US 2008/0097733 A1 Apr. 24, 2008

Related U.S. Application Data

(60) Provisional application No. 60/591,071, filed on Jul. 26, 2004.

(51) Int. Cl.
*G09B 23/28* (2006.01)
(52) U.S. Cl. ........................................................ 434/262
(58) Field of Classification Search .................... 434/262
See application file for complete search history.

(56) References Cited

U.S. PATENT DOCUMENTS

| | | | | |
|---|---|---|---|---|
| 5,014,262 A | * | 5/1991 | Harshavardhana | 370/237 |
| 5,390,256 A | * | 2/1995 | Mandell et al. | 381/77 |
| 6,031,987 A | * | 2/2000 | Damani et al. | 703/17 |
| 6,126,450 A | * | 10/2000 | Mukai et al. | 434/262 |
| 2001/0001852 A1 | * | 5/2001 | Rovinelli et al. | 703/22 |
| 2004/0044546 A1 | * | 3/2004 | Moore | 705/2 |

OTHER PUBLICATIONS

Tierney et al., "Computerizing Guidelines to Improve Care and Patient Outcomes: The Example of Heart Failure" Journel of American Med. Informatics, vol. 2, No. 5, 1995.

Lobach et al., "Development and Evaluation of a Computer-Assisted Management Protocol (CAMP); Improved Compliance with Care Guidelines for Diabetes Mellitus", Proceedings Annual Symposium on Computer Application, Nov. 1994.

Johnston et al., "Effects of Computer-Based clinical Decision Support Systems on Clinician Performance and Patient Outcome"., Jan. 15, 1994, vol. 120 (2).

Vee et al., Parallel Discrete Evene Simulation, Communication of the ACM., vol. 33(10) 1990.

Peleg et al, "Guideline Interchange Format 3.5 Technical Specification".

Shiffman et al., Computer-Based Guideline Implementation Systems: A Systematic Review of Functionality and Effectiveness. Journal of American Medical Informatics vol. 6 (2) 1999.

* cited by examiner

*Primary Examiner* — Xuan Thai
*Assistant Examiner* — Jerry-Daryl Fletcher

(57) ABSTRACT

A system and method are provided for performing a simulation of patient treatment using at least one executable clinical guideline. The method includes the steps of: providing for getting a selected start point associated with a step of a guideline, wherein the start point is selectable regardless of the actual treatment provided to the patient and condition of the patient; providing for accessing a guideline associated with the start point; and providing for performing a simulation. The simulation includes the steps of providing for processing the start point; providing for accessing the guideline having the step associated with the start point; and providing for executing at least the associated guideline including beginning execution at the start point.

22 Claims, 3 Drawing Sheets

Figure 1:
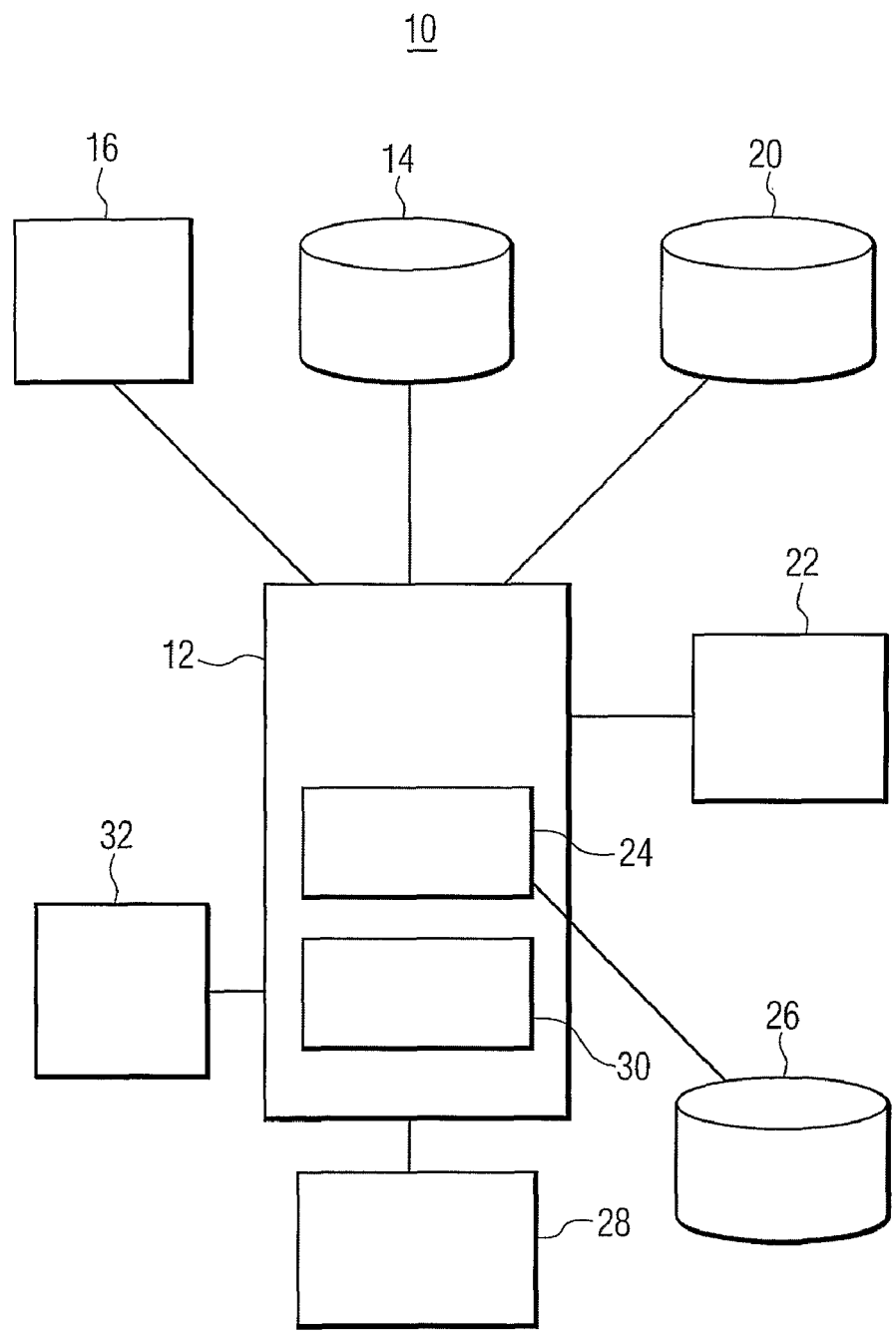

DECISION SUPPORT SYSTEM FOR SIMULATING EXECUTION OF AN EXECUTABLE CLINICAL GUIDELINE

The present invention relates generally to decision support systems, and more particularly to a decision support system for use in assisting in providing healthcare to a patient using executable clinical guidelines.

Existing evidence demonstrates that improvement of the effectiveness of patient care can be achieved by using computer based implementation of evidence based executable clinical practice guidelines integrated with clinical workflow. The improvement may include the ability to provide patient specific recommendations at points of care. The executable guidelines make knowledge readily available to the clinician, without the clinician having to seek out the specific knowledge. Many professional societies (e.g., ACP-ASIM, ACR, ACC, etc.) prepare guidelines for the care of patients. Using a current system, a clinician may access a guideline, and execute the guideline by starting at a first step of the guideline, and proceeding to follow steps of the guideline sequentially in accordance with the patient's treatment. However, the system does not provide the clinician with the ability to simulate procession through a series of steps, such as for exploring possible outcomes associated with a selected guideline or portion thereof.

The present invention is therefore directed to the problem of developing a system and method for providing a clinician with the ability to simulate procession through a series of steps of a selected guideline, or portion thereof, for determining possible outcomes associated with following the series of steps of the guideline.

It is an aspect of the present invention to provide a system and method for executing an executable clinical guideline for providing guidance in treating a patient. The individual guidelines include at least one step selected from at least one of an executable step and a state step. In one aspect of the invention, a computing system is provided having a guideline repository providing for storing a plurality of executable guidelines. At least one interface is provided for enabling entry of patient data associated with at least one of a patient and the patient's treatment and a start point associated with a step of a guideline of the plurality of guidelines. The computing system further includes a decision support system providing for performing a simulation including processing the start point, accessing the guideline having the step associated with the start point, and executing at least the associated guideline including beginning execution at the start point. The start point is selectable regardless of the actual treatment provided to the patient and condition of the patient In another aspect of the invention, a method is provided for performing a simulation of patient treatment using the at least one executable clinical guideline. The method includes the steps of: providing for getting a selected start point associated with a step of a guideline, wherein the start point is selectable regardless of the actual treatment provided to the patient and condition of the patient; providing for accessing a guideline associated with the start point; and providing for performing a simulation. The simulation includes the steps of providing for processing the start point; providing for accessing the guideline having the step associated with the start point; and providing for executing at least the associated guideline including beginning execution at the start point.

In another aspect of the invention, a computer data signal embodied in a transmission medium is provided. The data signal includes a code segment including instructions for providing for getting a selected start point associated with a step of a guideline, wherein the start point is selectable regardless of the actual treatment provided to the patient and condition of the patient; a code segment including instructions for accessing a guideline associated with the start point; and a code segment including instructions for performing a simulation, including a code segment including instructions for processing the start point. The latter code segment includes a code segment including instructions for accessing the guideline having the step associated with the start point; and a code segment including instructions for executing at least the associated guideline including beginning execution at the start point.

Figure 2:
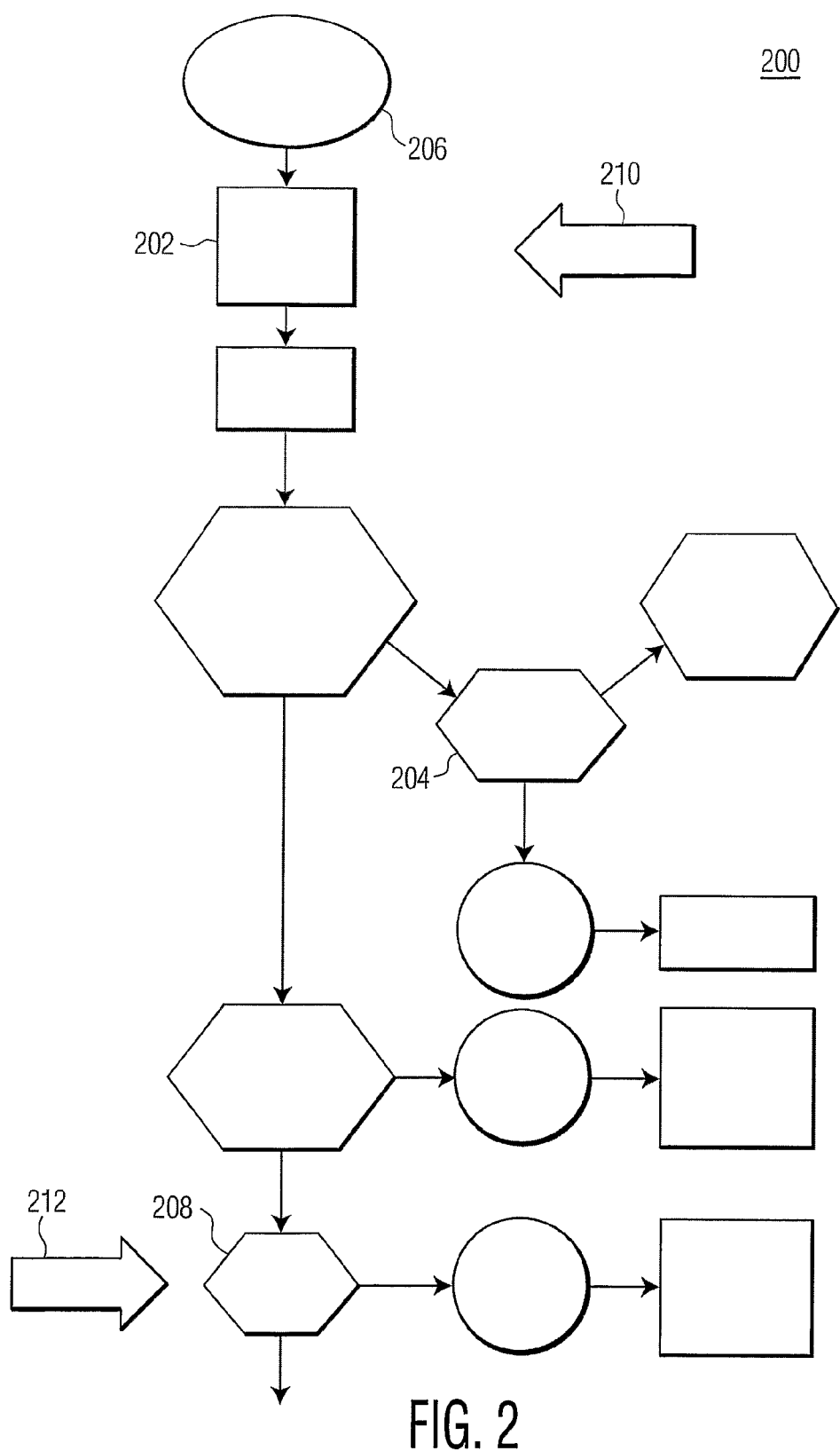
Figure 3:
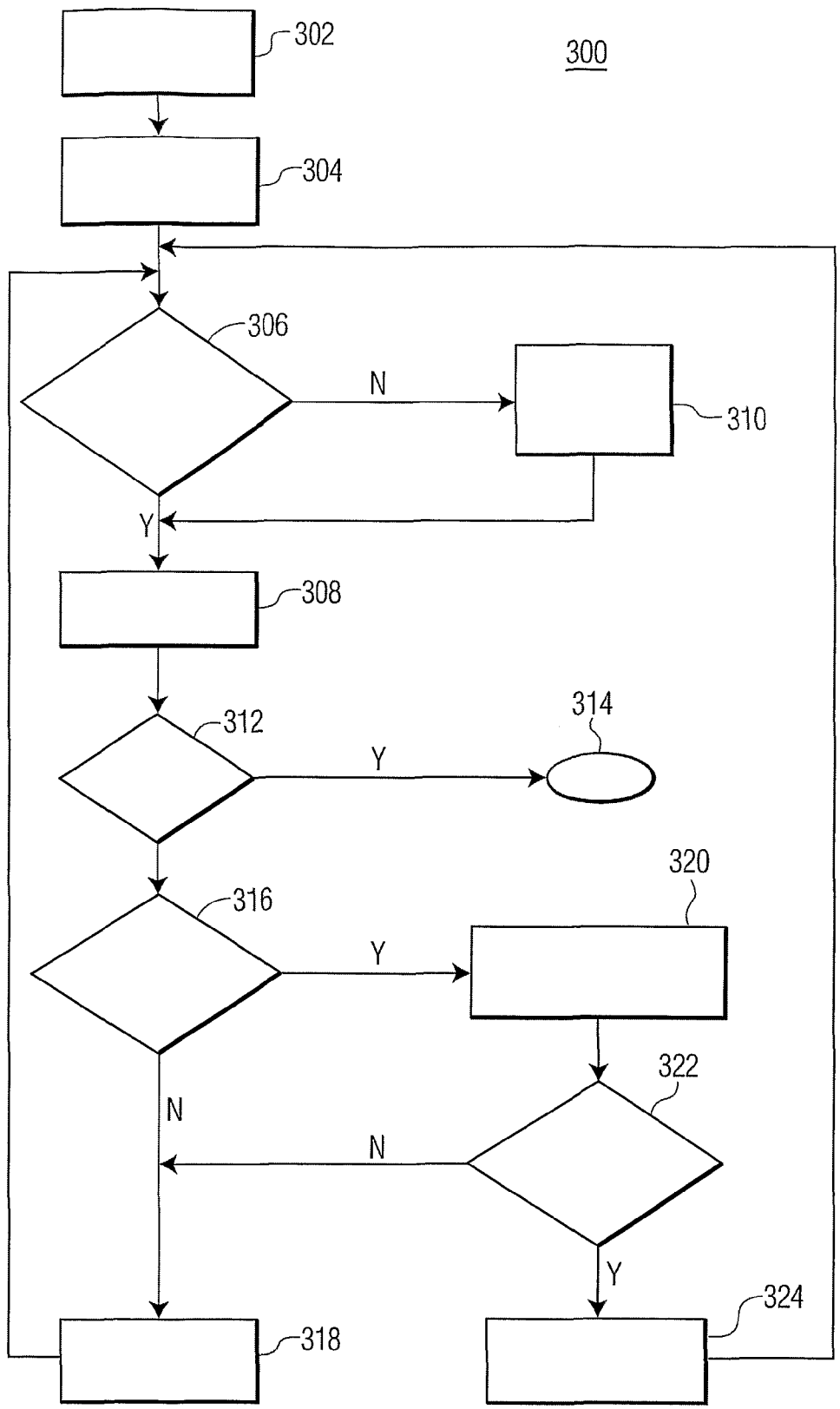

These and other features, aspects, and advantages of the present invention will become better understood with reference to the below listed drawings, and detailed description of the invention:

FIG. 1 is a block diagram of an exemplary clinical system in accordance with the present invention;

FIG. 2 graphical user interface of an exemplary executable clinical guideline in accordance with the present invention; and FIG. 3 is a flow chart showing steps of an exemplary simulation procedure in accordance with the present invention.

The present invention describes a decision support system which executes selected clinical guidelines for guiding a user in the treatment of a patient. The user may be, for example, a clinician, a nurse, a technician, or a hospital administrator. The respective guidelines include at least one step, such as, steps in which a decision is made based on, e.g., data relating to the patient and/or the patient's care; actions are taken by the decision support system; the patient state is described; and recommended actions are provided to the clinician. The user may simulate progression through one or more guidelines by indicating a start and end point for the simulation. During the simulation, as information is needed for executing the guidelines, the decision support system accesses data that is available and/or makes estimations for data that is not available. Preferably, the decision support system makes corrections when appropriate as data becomes available.

FIG. 1 shows an exemplary clinical system 10 for use in assisting in providing healthcare to a patient in accordance with the present invention. The term database refers to a structured storage, but is not limited thereto, and may further refer to a data source that is not structured, such as a repository. The system 10 is implemented using at least one processor and at least one storage medium accessible by the at least one processor. Components of the system 10 include the decision support system (DSS) 12; at least one database storing patient data including information relating to the patient and/or his treatment, such as a patient database 14 (such as for storing personal data relating to a plurality of patients) and a lab data database 16 (such as for storing results of lab tests performed on a plurality of patients); a guideline database 20; and a system user interface 22. The couplings between the components of the system 10 may be wired or wireless, and may be provided by one or more networks, such as a LAN, a WAN, an intranet, the Internet or a combination thereof.

The respective components of the system 10 may share resources of the at least one processor and the at least one storage medium, or may have exclusive use of one or more of the resources. The at least one processor may include, for example, a personal computer, a microprocessor, a handheld computing device, a server, etc. The at least one storage medium may include, for example, a hard drive, a CD-ROM, RAM, flash memory, volatile memory, non-volatile memory, etc.

The DSS 12 may reside on a server and/or storage accessible thereby for execution by the server, where the server is accessible by a plurality of computers. For example, a user, such as a clinician, may operate a workstation, such as a personal computer, in order to use the DSS 12, where execution of the DSS 12 is performed at the server or at the workstation. Alternatively, the DSS may reside on one or more workstations and/or storage devices accessible thereby for execution by the work station.

Furthermore, the DSS may be embedded within or linked to another system, such as an administrative information system (e.g., for a hospital, nursing home, laboratory, etc.). Exemplary applications for the DSS include assistance in resource management and/or planning and/or quality assurance.

The DSS 12 may access a selected guideline from the guideline database 20, where the guideline is selected for appropriately guiding the user in the patient's current treatment. The guideline may be selected by the user by instructing the DSS 12 to access the selected guideline, or the guideline may be selected by the DSS 12 in accordance with clinical context related data available to the DSS 12, such as the context of the patient's present state, medical history, care provided so far, etc. A clinical application having the necessary interfaces may be used to submit patient data including clinical context data to the DSS 12, or the system user interface 22 may be used to allow the user to enter patient data. A copy of the selected guideline or links thereto may be stored temporarily or permanently, such as at the user's work station, with the patient's data in the patient database 14, and/or in a workspace provided by and/or accessible by the guideline database 20 or the DSS 12. The stored copy may be customized for the individual, such as by eliminating or bypassing certain steps of the guideline. For example, a clinician may use a guideline editing tool to create a personalized version of the guideline.

The guideline database 20 stores a plurality of guidelines. Respective guidelines include at least one step, usually forming at least one series of steps. The guidelines stored in the guideline database 20 are preferably evidence-based, and developed in accordance with experience and research of experts in the field. The guidelines are encoded by appropriate encodings, such as ASBRU, GLIF, EON, GUIDE, PRODIGY and PROforma, etc. The guideline database 20 is preferably searchable for finding and selecting a particular guideline or the guideline that best meets criteria for guidance in the patient's current treatment, or for simulation of treatment of the patient. The guideline is typically selected to provide clinical guidance for treatment within a context best matching a combination of at least one of a patient context, user context, care context, etc.

Interaction between the DSS 12 and the user is provided via the system user interface 22. The system user interface 22 preferably includes a guideline interface, which presents a representation of the guideline being executed to the user. The guideline user interface may include a display, such as for a handheld or desktop computing device, a pointing device and/or a keyboard, etc. The guideline user interface may include a graphical user interface (GUI), but need not be graphical. For example, a telephone voice activated system that uses voice recognition technology may be used, and/or menu choices and/or prompts may be audio messages. User responses may be provided by key pushes and/or voice responses.

Preferably the guideline user interface provides an indication of the guideline and step presently being executed. Via the guideline user interface the user may select a start point and end point for a simulation. The start point and end point are each associated with a step of a guideline, and may be associated with steps from different guidelines or the same guideline. The start point and end points may be selected regardless of the actual treatment provided to the patient and condition of the patient.

Execution begins at the start point for stepping through one or more guidelines by beginning at the start point, even when the actual care of the patient is not performed in accordance with the guideline(s) being simulated. The end point may be selected before the simulation or during the simulation. Selection of the start point and end point may be by the user and/or by fulfillment of a condition. Furthermore, the user may select one or more steps of the guideline(s) to be skipped or altered during the simulation, such as by using a guideline editing tool. Representations of the selected start and/or end points are presented to the user by the guideline user interface for reference during the simulation, if possible. For example, the display may show sequentially or simultaneously the one or more guidelines which are to be included in the simulation procedure, and show the start point and/or end point, such as by different colored arrows. It is possible that not all guidelines to be executed during the simulation will be known from the beginning, as decision(s) made during execution of the guideline(s) may affect which guidelines will be executed. The actual step which corresponds to the end point may not be known during the entire simulation procedure, and may be determined during or at the end of the simulation procedure. Accordingly, the end point is displayed when it is known.

The start and end points may be specified by the user by specifying the guideline (particularly if different from a current selected guideline) and step in which the respective start and end points reside. Other methods of indicating start and end points include specifying a patient state, using a GUI to point and start to a step, specifying a condition, starting and/or terminating "live" at a current point of execution, etc., or a combination thereof, such as in accordance with predetermined or specified precedence orders.

The start point may include a set of selectable start points, and execution is begun at a selected start point of the set of selectable start points. The selected start point is selected in accordance with fulfillment of a condition, where the condition may be predetermined or entered by a user. Likewise, the end point may include a set of selectable end points, and execution is terminated at a selected end point of the set of selectable end points, wherein the selected end point is selected in accordance with fulfillment of a condition, wherein the condition may be predetermined or entered by a user. For example, the start point or end point may be a patient state, completion of a guideline, a specific step of a specific guideline, determined by a logic expression, or a combination thereof.

An exemplary GUI for a guideline 200 is shown in FIG. 2. The individual steps of the guideline 200 include a variety of types of steps, including an action step exemplified by step 202, instructing a clinician or a component of the system 10 that an action be taken (such as, gathering information, performing tests, providing treatment, or jumping to another step of the guideline or of a different guideline); a choice step exemplified by step 204 for prompting a user to decide the next step to perform from at least two steps; a patient state step exemplified by step 206 representing the current state of the patient or a patient related condition; and a case step exemplified by step 208, at which at least one algorithm is performed for deciding which step to perform next.

The GUI shown represents the guideline 200 as a flowchart. The GUI may represent the guideline in other formats, for example as a text document. An indicator, such as arrow 210 is displayed to show the current step being processed during execution of the guideline. An indicator, such as arrow 212, is displayed to show the selected start step for performing the simulation. Likewise, an indicator may be provided for showing the selected end step. If more than one start or end step are entered, and selection is to be performed, such as in accordance with a condition, event, result of an algorithm, etc., then the entered start and/or end points may be shown, and/or the start and end points may be shown upon selection thereof. Preferably, the indicator used distinguishes between entered points and selected points. Individual steps or guidelines may have at least one associated rating indicating the quality of the data, research, experimental methodology, support by experts in the field, etc., associated with the step. Preferably, the associated rating is selectably viewable on the GUI 200.

The DSS 12 performs the simulation by controlling progression through the guideline(s), including accessing the guideline having the step associated with the start point, beginning execution at the start point, and terminating at the end point. Performance of the simulation includes accessing available data as needed during the simulation from the appropriate sources, such as by prompting the user for a response, accessing the at least one database (such as the patient database 14, lab database 16), storing information relating to the patient and/or his care, and/or accessing one or more databases or knowledge bases storing non-patient specific knowledge, such as the general data source 32. The simulation may be, for example, a parallel discrete event simulation employing a "time warp mechanism".

The system user interface 22 may provide information to the user during or at the end of the simulation, such as in the format of a display. The information provided to the user may include the last step performed, the patient's state at the current point of the simulation, the suggested next step, and/or a prompt to the user asking how would the user like to proceed.

With respect to the preferred embodiment shown in FIG. 1, the DSS 12 may further include (or access) an assumption module 24 for providing simulated data when data needed during the simulation is not available. The simulated data values may be determined by providing a default value, performing an algorithm, and/or executing an equation, which may include using data that is available. The assumption module 24 may access an assumption database 26 for accessing stored default values, equations and/or algorithms for providing the simulated data values. The assumption module 24 preferably provides a quantitative or qualitative indicator of the degree of certainty for individual instances of provision of simulated data. The indicator of degree of certainty may, for example, refer to the method used for determining the simulated data values, a source for the simulated data values, and/or a statistical value indicating statistics for historical experience related to the simulated data and the value used. It is also envisioned that the assumption module will query the user when data is not available. The user may provide the data or an estimate thereof, or request that the DSS 12 determine the value(s) for the simulated data.

It is further envisioned that the DSS 12 report during the simulation and/or after the simulation which data was simulated. The report may include the indicator of the degree of certainty for the simulated data.

In accordance with the preferred embodiment shown in FIG. 1, the system 10 further includes an event notification server 28 which notifies the DSS 12 as to when data becomes available. The event notification server 28 may check the appropriate databases, such as the patient database 14 or the lab database 16, for new data. The new data may include newly available data and/or updates to data that had not been previously available and/or to data that had been used, which is now stale data. A variety of methods may be used for checking for new data, including synchronous or asynchronous polling (e.g., event triggered), and/or notification by the databases. Upon sensing receipt of new data, the event notification server 28 may determine if the new data includes specific data of interest. Upon determining that new data (or specific new data) is available, the event notification server 28 may set a flag or otherwise alert the CDSS 12.

In accordance with the preferred embodiment shown in FIG. 1, the system 10 further includes a rollback module 30 which determines when and if rollback is to be performed, and controls rollback of the simulation for the purpose of using new data. The rollback module 30 is notified when new data is available. The rollback module 30 determines if a rollback procedure will be performed, such as by determining if the new data corresponds to simulated data, other data expected to be used during the simulation, and/or other data already used during the simulation (e.g., stale data). Furthermore, the rollback module 30 may determine if the rollback procedure will be performed if the difference between or ratio of the new data (or a portion thereof) and the original value (which may be simulated data and/or stale data) exceeds a predetermined threshold. The predetermined threshold may vary for different data. Rollback may be performed for a portion of the new data or all of the new data.

The rollback procedure may be performed immediately upon notification of the availability of new data, at the conclusion of an event or at the conclusion of the simulation. Upon performance of a rollback procedure, the DSS 12 may perform a rollback procedure by rolling back to a point of the simulation at which the simulated data and/or stale data was processed (preferably first processed), which is herein referred to as the rollback point. The guideline(s) included in the simulation is re-executed from the rollback point using the new data.

A flowchart 300 is shown in FIG. 3, illustrating the steps of an exemplary simulation procedure. At step 302, the DSS 12 gets the start and/or end points. At step 304, the simulation begins by proceeding to the guideline and step indicated by the start point. At step 306, the DSS 12 determines if any data are needed to perform the current step of the simulation, and if so, determines if the data are available. If the data was available, control passes to step 308, where the current step is performed using the available data if applicable. If the data are not available, step 310 is performed, where a data assumption operation is performed by the data assumption module 24 for providing simulated data, after which control passes to step 308. At step 308, the current step is performed using the simulated data.

At step 312, a determination is made if the end point has been reached and if the simulation should be ended. If "yes", control passes to step 314 to end the simulation, at which point a report and/or display may be provided to the user, and/or a prompt for what to do next. If "no", control passes to step 316. At step 316, a determination is made if an event notification has occurred or if new data are available that corresponds to data needed for processing the next step(s). If "no", control passes to step 318, where execution of the guideline is advanced to the next step by assigning the next step of the guideline to be the current step. Execution of step 318 is followed by execution of step 306 for determining if all data needed to perform the current step is available. If the determination made at step 316 is "yes", control passes to step 320, where the new data (e.g., the newly available or updated data) are retrieved.

The new data retrieved may be all of the available new data or a subset thereof, such as only the new data which are to be processed in the next step(s) and/or was processed in the previous step(s). Next, control passes to step 322, where a determination is made if a rollback procedure is to be performed. If "yes", control passes to step 324, where the rollback module 30 determines a new current step (e.g., the rollback point). Execution of step 324 is followed by execution of step 306 for determining if all data needed to perform the current step is available. If the determination made at step 322 is "no", control passes to step 318 for advancing to the next step of the guideline.

In accordance with results obtained during or upon completion of at least a portion of the simulation procedure, the simulation procedure may further include making recommendations for and/or providing for treatment of the patient in accordance with the simulation, e.g., including using the values of the simulated data. It is contemplated that the simulation may be run more than one time by changing at least one parameter of the simulated data, such as by a predetermined or calculated increment (or decrement) for each iteration of the simulation and/or changing decisions made, e.g., at case or action step(s). The results of the simulation iterations, or portions thereof, can be compared to one another and/or to target results. A determination may be made as to which simulation data parameters and/or decisions produce the best results or the desired results. Treatment for the patient may be carried out accordingly.

It is contemplated that guidelines stored in the guidelines database 20 may be updated, and that the system 10 includes a guideline update notification which notifies the DSS 12 when a guideline update occurs, or the DSS 12 checks with the guideline update notification to determine when an update occurs. Upon determination of a guideline update, the DSS 12 and/or the user are notified. The DSS 12 may restart a guideline that is being executed, or rollback to a point at which the update might effect results. The restart procedure and/or rollback procedure may be performed via user intervention. It is further contemplated that simulation be provided for the control of ambient intelligent environments for situations in which data used for controlling an ambient intelligent environment is not available.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

The invention claimed is:

1. A computing system for executing an executable clinical guideline for providing guidance in treating a patient, the computing system comprising:
   a guideline repository providing for storing a plurality of executable guidelines, wherein individual guidelines of the plurality of guidelines include at least one step selected from at least one of an executable step and a state step;
   at least one interface providing for enabling entry of patient data associated with at least one of a patient and the patient's treatment and a start point associated with a step of the at least one step of a guideline of the plurality of guidelines, wherein the start point is selectable regardless of the actual treatment provided to the patient and condition of the patient and the start point does not correspond to a first point of a first of the plurality of executable guidelines; and
   a decision support system providing for performing a simulation including processing the start point, accessing the guideline having the step associated with the start point, and executing at least the associated guideline including beginning execution at the start point,
   wherein the plurality of executable guidelines are computer readable and executable instructions that are automatically read and executed by the decision support system while performing the simulation without user interaction.

2. The computing system of claim 1, wherein the decision support system automatically selects the guideline having the step associated with the start point without user interaction and based on a clinical context of the patient.

3. The computing system of claim 2, wherein the decision support system comprises an assumption module providing for determining if the selected data to be retrieved from the at least one data source are available, and if not available providing simulated data having values determined by at least one of a default value, performing an algorithm and executing an equation.

4. The computing system of claim 3, further comprising an assumption database providing for storing assumption data including at least one of default values, equations and algorithms; and wherein the assumption module accesses the assumption database to retrieve assumption data for determining the simulated data values.

5. The computing system of claim 3, wherein the assumption module provides for generating a query to a user for obtaining data to be used for determining the values of the simulated data.

6. The computing system of claim 3, wherein the assumption module provides for providing an indicator of degree of certainty for respective simulated data values indicating at least one of a method used for determining the simulated data values, a source for the simulated data values, and statistics for historical experience related to the respective determined simulated data values.

7. The computing system of claim 2, further comprising an event notification server, wherein:
   the decision support system provides for determining if the selected data to be retrieved from the at least one data source are available;
   the event notification server provides for notifying the decision support system upon the availability of new data via the at least one data source, and
   when the new data are usable for the selected data that was determined to be not available, the decision support system provides for processing the new data including providing for using the new data for providing the selected data that was not available for use in execution of the at least one associated guideline.

8. The computing system of claim 2, further comprising an event notification server, wherein:
   the event notification server provides for notifying the decision support system upon the availability of new data via the at least one data source, and
   the decision support system further comprises a rollback module for providing for controlling rollback of the simulation for rolling back the simulation to a point of the simulation at which data that corresponds to the new data was used, and providing for re-executing the at least one associated guideline from the point of the simulation.

9. The computing system of claim 8, wherein the rollback controlled by the rollback module is performed as a time warp simulation.

10. The computing system of claim 1, wherein the at least one interface further enables entry of an end point associated with a step of the at least one step of a guideline of the plurality of guidelines, wherein the end point does not correspond to a last point of a last of the plurality of executable guidelines, and wherein performance of the simulation further includes processing the end point and terminating execution of the at least the associated guideline upon executing the step associated with the end point.

11. The computing system of claim 1, wherein the at least one interface includes a user interface for enabling a user to enter data including at least a portion of the patient data, the start point and the end point.

12. The computing system of claim 1, wherein the start point includes a set of at least two selectable start points, and execution is begun at a selected start point of the at least two selectable start points, wherein the selected start point is selected by the decision support system in accordance with at least one of fulfillment of a condition.

13. The computing system of claim 1, wherein the end point includes a set of at least two selectable end points, and execution is terminated at a selected end point of the at least two selectable end points, wherein the selected end point is selected by the decision support system in accordance with at least one of fulfillment of a condition.

14. The computing system of claim 1, wherein the simulation performed is a discrete event simulation.

15. A method for performing a simulation of patient treatment using at least one executable clinical guideline selectable from a plurality of guidelines, the respective guidelines having at least one step selected from at least one of an executable step and a state step, the method comprising the computer implemented steps of:
providing for getting a selected start point associated with a step of the at least one step of a guideline of the plurality of guidelines, wherein the start point is selectable regardless of the actual treatment provided to the patient and condition of the patient;
providing for accessing a guideline associated with the start point; and
providing, via a processor, for performing a simulation comprising the steps of:
providing for processing the start point;
providing for accessing the guideline having the step associated with the start point; and
providing for executing at least the associated guideline including beginning execution at the start point, wherein the plurality guidelines are computer readable and executable instructions that are automatically read and executed by the processor while performing the simulation without user interaction.

16. The method according to claim 15, further comprising the steps of:
providing for getting an end point associated with a step of the at least one step of a guideline of the plurality of guidelines; and
providing for terminating the simulation, comprising the steps of:
providing for processing the end point; and
providing for terminating execution of the at least the associated guideline upon executing the step associated with the end point.

17. The method according to claim 15, wherein the executing step includes the step of providing for retrieving selected data from at least one data source.

18. The method according to claim 17, wherein the retrieving step comprises:
providing for determining if the selected data to be retrieved from the at least one data source are available; and
providing for generating simulated data having values determined by at least one of a default value, performing an algorithm and executing an equation, if not available.

19. The method according to claim 18, wherein the providing simulated data step comprises the step of providing for providing an indicator of degree of certainty for respective simulated data values indicating at least one of a method used for determining the simulated data values, a source for the simulated data values, and statistics for historical experience related to the respective determined simulated data values.

20. The method according to claim 18, further comprising
providing for generating a notification upon the availability of new data via the at least one data source; and
providing for controlling rollback of the simulation for rolling back performance of the simulation to a point of the simulation at which data corresponding to the new data was used, including providing for re-executing the at least one associated guideline from the point of the simulation.

21. The method according to claim 15, further comprising the step of providing for treating the patient in accordance with the simulation, including using the values of the simulated data.

22. Computer data, embodied in a storage medium, which when executed by a processor, causes the processor to perform a simulation of patient treatment using at least one executable clinical guideline selectable from a plurality of guidelines, the respective guidelines having at least one step selected from at least one of an executable step and a state step, the data comprising:
a code segment including instructions for providing for getting a selected start point associated with a step of the at least one step of a guideline of the plurality of guidelines, wherein the start point is selectable regardless of the actual treatment provided to the patient and condition of the patient;
a code segment including instructions for providing for accessing a guideline associated with the start point; and
a code segment including instructions for providing for performing a simulation, the code segment including:
a code segment including instructions for providing for processing the start point;
a code segment including instructions for providing for accessing the guideline having the step associated with the start point; and
a code segment including instructions for providing for executing at least the associated guideline including beginning execution at the start point, wherein the plurality guidelines are computer readable and executable instructions that are automatically read and executed by the processor while performing the simulation without user interaction.

* * * * *